United States Patent
Reinpoldt

(10) Patent No.: US 8,519,850 B2
(45) Date of Patent: Aug. 27, 2013

(54) METHOD AND SYSTEM FOR THE ACQUISITION, TRANSMISSION AND ASSESSMENT OF REMOTE SENSOR DATA FOR TREND ANALYSIS, PREDICTION AND REMEDIATION

(75) Inventor: Michael A. Reinpoldt, Windermere, FL (US)

(73) Assignee: Thermal Matrix USA, Inc., Tampa, FL (US)

( * ) Notice: Subject to any disclaimer, the term of this patent is extended or adjusted under 35 U.S.C. 154(b) by 220 days.

(21) Appl. No.: 13/019,123

(22) Filed: Feb. 1, 2011

(65) Prior Publication Data

US 2012/0194342 A1 Aug. 2, 2012

(51) Int. Cl.
G08B 23/00 (2006.01)

(52) U.S. Cl.
USPC .............. 340/573.1; 340/539.12; 340/539.26; 340/539.1; 340/584; 340/588; 340/589

(58) Field of Classification Search
USPC ...................................................... 340/573.1
See application file for complete search history.

(56) References Cited

U.S. PATENT DOCUMENTS

2004/0116822 A1* 6/2004 Lindsey ......................... 600/549
2008/0091471 A1* 4/2008 Michon et al. ..................... 705/3
2010/0105427 A1* 4/2010 Gupta ......................... 455/556.1

* cited by examiner

*Primary Examiner* — Daniel Wu
*Assistant Examiner* — Anthony D Afrifa-Kyei
(74) *Attorney, Agent, or Firm* — McKinney Law, PLLC

(57) ABSTRACT

A method to analyze the spread of viral or bacterial infections in a population using remote thermal sensor data is disclosed. The method includes determining a body temperature of passengers traveling through a public transportation facility using a remote thermal sensor, storing the body temperatures of the passengers in a database, assigning at least one geographic characteristic to the stored body temperatures in the database, and comparing the body temperatures to a known normal body temperature of humans. In addition, the method includes generating an alert when the body temperatures of the passengers are above the normal body temperature to indicate an illness. The at least one geographic characteristic may be an origination location, destination location, or any combination thereof. The method also includes accessing flight information stored on a remote server, and correlating the flight information to the passengers.

17 Claims, 5 Drawing Sheets

METHOD AND SYSTEM FOR THE ACQUISITION, TRANSMISSION AND ASSESSMENT OF REMOTE SENSOR DATA FOR TREND ANALYSIS, PREDICTION AND REMEDIATION

I. FIELD

The present invention relates in general to the fields of automated temperature detection and remote data collection and assessment, and in particular to the interfacing of real-time and collected thermal sensor data to existing database information, and methods for acquiring, analyzing, manipulating, and drawing correlations between sensor data and stored information for the purpose of identifying and predicting trends.

II. DESCRIPTION OF RELATED ART

Viral transmittal of flu and sickness has been a continual problem especially in mass transit situations where crowds of strangers intermingle in close proximity from and to different destinations. Remote, non-contact temperature monitoring equipment has recently become available to detect elevated forehead temperatures of passengers. This monitoring equipment typically yields individualized results without recording or memorializing the sensor data.

Additionally, it has become standard for real-time and stored or recorded sensor data to be interfaced to computer systems. Sensor data is traditionally comprised of various elements that describe an individual, object, or environment. These elements can be stored and analyzed by computer software to provide specific results, or react to specific inputs, allowing actions to be performed through direct manipulation of the sensor data.

It has become common to collect, collate, and store data in a way that can be easily accessed by a computer. This data can be comprised of various elements that describe a person, object, environment, function, feature, or event. This data can be stored in such a way as to provide specific data as well as associated data related to a specific element, and to allow the recall of the information.

Accordingly, there is a need in the relevant art for a system and method that gives the user the ability to manipulate and derive new information from the acquisition, transmission, and assessment of remote sensor data merged or combined with existing data from a previously stored database.

There is also a need in the art for a system and method that algorithmically analyses and derives new information from the acquisition, transmission, and assessment of remote sensor data merged or combined with existing data from a previously stored database.

There is also a need in the art for a system and method that allows for trends to be ascertained from the acquisition, transmission, and assessment of remote sensor data merged or combined with existing data from a previously stored database.

There is also a need in the art for a system and method that allows predictions to be drawn from the acquisition, transmission, and assessment of remote sensor data merged or combined with existing data from a previously stored database.

Another need exists in the art for a system and method that implements the combined functionality upon real-time, stored or recorded sensor data and previously stored data.

Yet another need exists in the art for a system and method that implements the aforementioned functionality for remote, non-contact, elevated temperature data from passengers in mass transit environments, collects and assesses such data, and autonomously tracks sources of sickness and predicts destinations of afflicted passengers.

However, in view of the prior art at the time the present invention was made, it was not obvious to those of ordinary skill in the pertinent art how the identified needs could be fulfilled.

III. SUMMARY

In a particular embodiment, a method to analyze the spread of viral or bacterial infections in a population using remote thermal sensor data is disclosed. The method includes determining a body temperature of at least one passenger traveling through a public transportation facility using a remote thermal sensor, storing the body temperature of the at least one passenger in a database, assigning at least one geographic characteristic to the stored body temperature in the database, and comparing the body temperature of the at least one passenger to a known normal body temperature of humans.

In addition, the method includes generating an alert when the body temperature of the at least one passenger is above the normal body temperature to indicate an illness. The at least one geographic characteristic is an origination location, destination location, or any combination thereof. The method also includes determining the at least one geographic characteristic by accessing flight information stored on a remote server, and correlating the flight information to the at least one passenger and adjusting the known normal body temperature of humans based on a time of day when determining the body temperature of the at least one passenger traveling through the public facility. The known normal body temperature is increased for afternoon and evening time of day over morning time of day. Further, the method includes comparing relative body temperatures of passengers from one specific point of departure with passengers from a different point of departure and comparing relative body temperatures of passengers from one specific point of departure with passengers from a same point of departure who arrived earlier or later. The method also includes comparing relative body temperatures of passengers from multiple points of departure, and collating a percentage of passengers from varying points of departure with variations in body temperature.

A real-time, non-contact thermal sensor may be used to gather skin/body temperature readings from air travel passengers exiting flights as they arrive at their destination. The real time sensor data, in conjunction with existing flight information stored in the airline's database, is used to collate elevated passenger temperatures with point of departure. This method further includes the ability to compare the relative temperatures of passengers from specific points of departure by time of day.

In another particular embodiment, a system to analyze the spread of viral or bacterial infections in a population using remote thermal sensor data is disclosed. The system includes a remote thermal sensor to collect body temperatures of passengers traveling through a public transportation facility, a database to store the body temperatures, a tracking module to track an origination location, destination location, or any combination thereof, of the passengers, a correlation module to correlate the body temperatures to the origination location, destination location, or any combination thereof, of the passengers, and an analysis module to predict trends of viral or bacterial infections based on the body temperatures and the origination location, destination location, or any combination thereof, of the passengers. The correlation module compares relative body temperatures of passengers from one specific point of departure with passengers from a same point of departure who arrived earlier or later.

One particular advantage provided by embodiments of the method and system to analyze the spread of viral or bacterial infections in a population using remote thermal data is the ability to compare the relative temperatures of passengers from multiple points of departure and collate the percentage of passengers from varying points of departure with variations in skin temperature. This includes the ability to compare skin temperature with the relative seating of passengers within the aircraft and the ability to predict which points of departure and points of destination will result in projected evaluated skin temperatures. Further, the embodiments include the ability to determine the outbreak of flu in at specific points of departure and destinations and to determine the likelihood of elevated skin temperature or contamination within an aircraft. Another particular advantage is the ability to predict and track the progression of elevated skin temperature or contamination between destinations.

Other aspects, advantages, and features of the present disclosure will become apparent after review of the entire application, including the following sections: Brief Description of the Drawings, Detailed Description, and the Claims.

IV. BRIEF DESCRIPTION OF THE DRAWINGS

V. DETAILED DESCRIPTION

As disclosed below, a method and system is disclosed to analyze a spread of viral or bacterial infections in a population using remote thermal sensor data. The method and system provides the ability to manipulate and derive new information from the acquisition, transmission, and assessment of the remote thermal sensor data merged or combined with existing data from a previously stored database.

Figure 1:
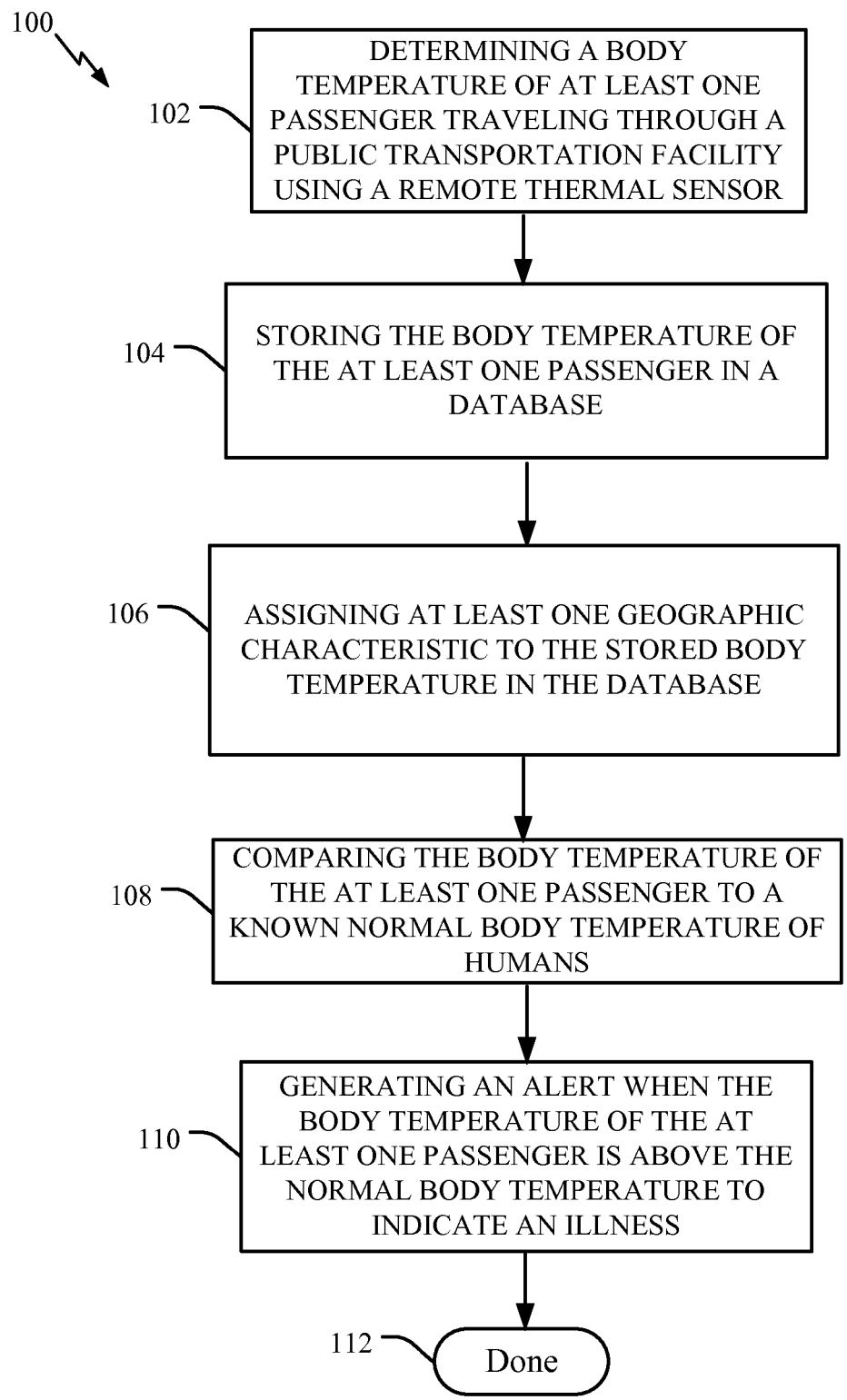
FIG. 1 is a flow diagram of a particular embodiment of a method to analyze a spread of viral or bacterial infections in a population using remote thermal sensor data.

A flow diagram of a particular embodiment of a method to analyze the spread of viral or bacterial infections in a population using remote thermal sensor data is described in FIG. 1 and generally designated 100. At 102, a body temperature of at least one passenger traveling through a public transportation facility using a remote thermal sensor is determined The body temperature of the at least one passenger is stored, at 104. Moving to 106, at least one geographic characteristic is assigned to the stored body temperature in the database. The body temperature of the at least one passenger, at 108, is compared to a known normal body temperature of humans. At 110, an alert is generated when the body temperature of the at least one passenger is above the normal body temperature to indicate an illness.

Figure 2:
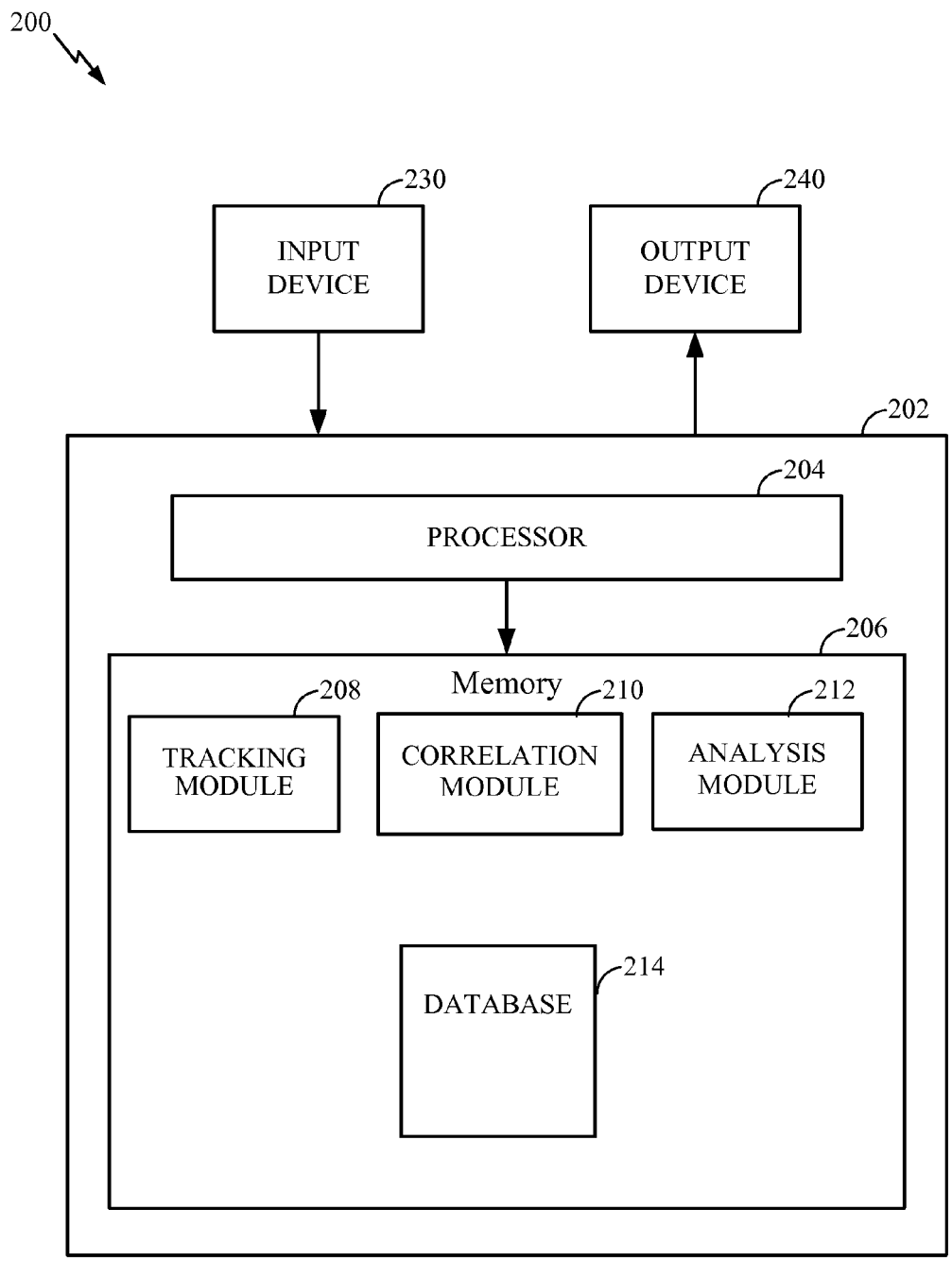
FIG. 2 is a block diagram of a particular illustrative embodiment of a system to analyze a spread of viral or bacterial infections in a population using remote thermal sensor data.

Referring to FIG. 2, a particular illustrative embodiment of a system to analyze a spread of viral or bacterial infections in a population using remote thermal sensor data is depicted and generally designated 200. The system 200 includes a processor 204 that is communication with an input device 230, where a memory 206 of a server 202 may be adapted to store a database 218 of body temperatures from remote thermal sensors and known normal body temperatures for comparing. A tracking module 208 may be used to track an origination location, destination location, or any combination thereof, of the passenger. A correlation module 210 may be used to correlate the body temperatures to the origination location, destination location, or any combination thereof, of the passengers. An analysis module 212 may be used to predict trends of viral or bacterial infections based on the body temperatures and the origination location, destination location, or any combination thereof, of the passengers. The correlation module 210 may compare relative body temperatures of passengers from one specific point of departure with passengers from a same point of departure who arrived earlier or later.

Figure 3:
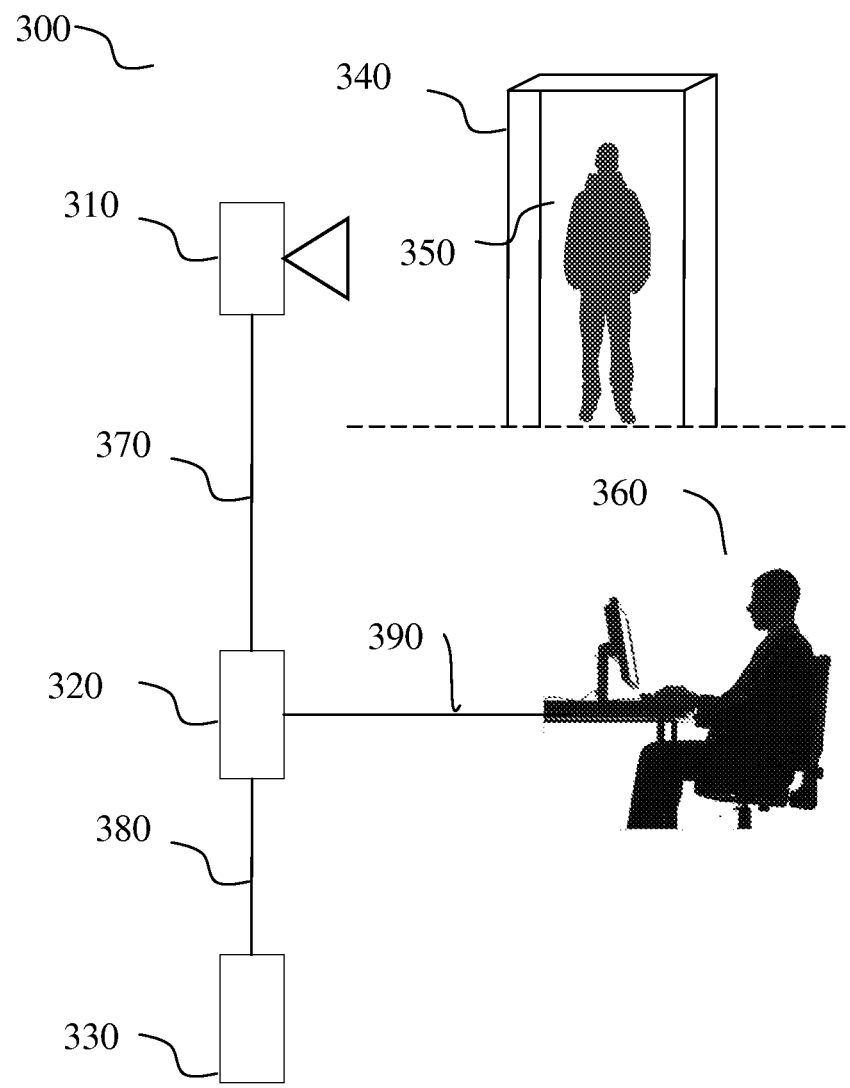
FIG. 3 is a block diagram of a particular embodiment of a system to analyze, manipulate and correlate real-time thermal sensor data of passengers with an airline database system to identify trends and predict viral contamination.

A block diagram of a particular embodiment of a system is disclosed in FIG. 3 and generally designated 300. The disclosed system employs a real-time, non-contact thermal sensor used to gather skin temperature readings from air travel passengers exiting flights as they arrive at their destination and utilizes this sensor data, in conjunction with existing flight information stored in the airline's database, to collate elevated passenger temperatures with point of departure. The system 300 includes a real-time thermal sensing device (sensor) 310 providing data to a database 320 which is also connected to the airline's server and database system 330. The real-time thermal sensor 310 captures and transmits the skin or body temperature readings of passengers 350 as they exit an aircraft's arrival gate 340. The real-time temperature data is collected, analyzed, and collated with the airline's server and database system 330 to the database 320. The database 320 manipulates data from the real-time thermal sensor 310 and the airline host server and database system 330 so as to provide, track, assess and predict outputs to an operator or user 360.

Interconnections 370, 380 and 390 are computer/data connection systems used to transmit and receive data between devices. Interconnections 370, 380 and 390 may be implemented using, but not limited to, the following techniques; RS-232, RS-422, RS-423, RS-488, AppleTalk, LocalTalk, Ethernet, wireless Ethernet, 802.11.

Figure 4:
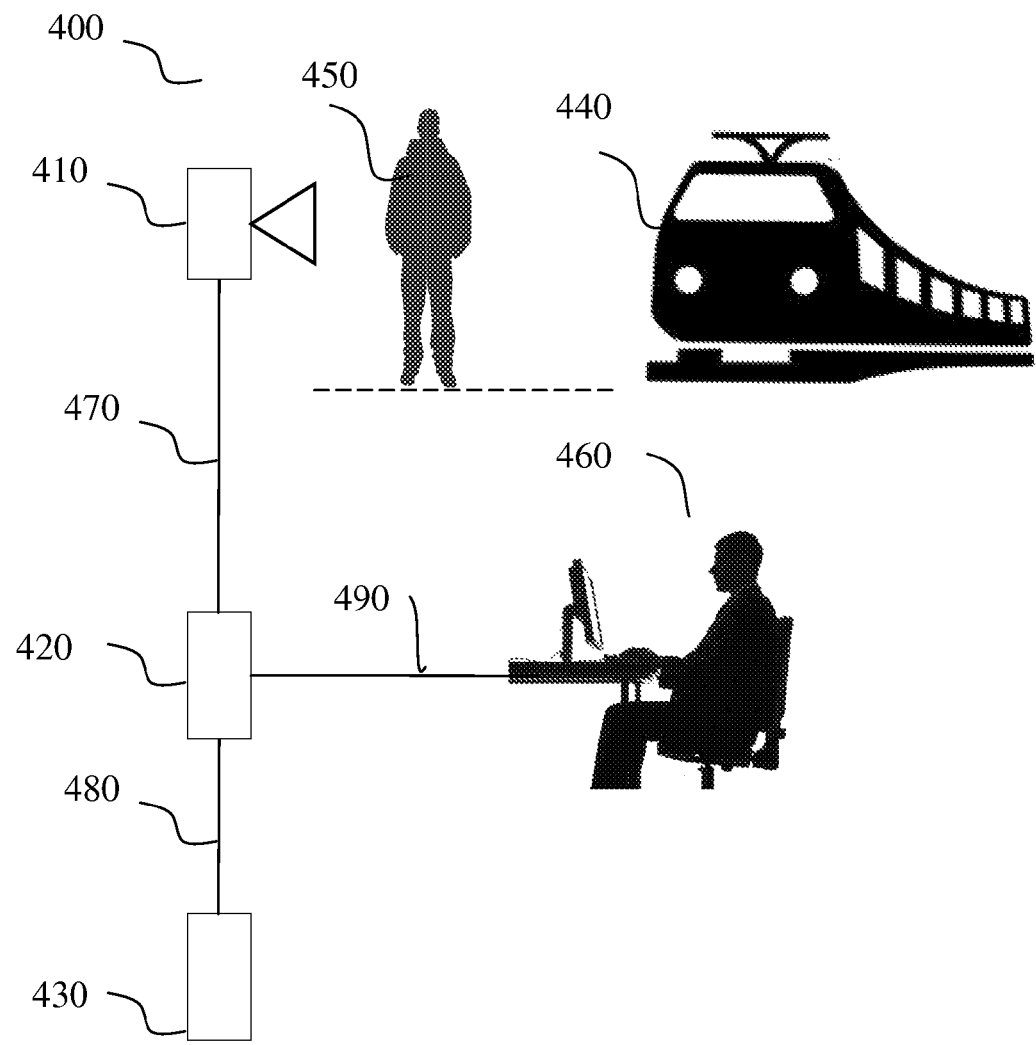
FIG. 4 is a block diagram of a particular embodiment of a system to analyze, manipulate and correlate real-time video surveillance system data and thermal sensor data with a mass-transit system database to identify trends and predict the movement and actions of passengers.

A block diagram of a particular embodiment of a system is disclosed in FIG. 4 and generally designated 400. The system 400 includes a real-time security system used to gather information on passengers of a mass transit system and utilizes this video data, in conjunction with existing information stored in the mass-transit database, to elevated passenger activity, times of departure and direction of travel. The system 400 includes a real-time video security system and thermal sensors 410 for providing data to a database 420 which is also connected to the mass-transit system's server and database system 430.

The real-time video security system 410 captures and transmits the actions and movements of passengers 450 as they stand, approach or depart the transit vehicles 440. The real-time video security system 410 data is collected, analyzed, and collated with the mass-transit system's server and database system 430 in the database 420, including thermal data of passengers.

The database 420 manipulates and correlates information from the real-time video security system 410 and the mass-transit database 430 so as to provide, track, assess and predict further movement or activity to an operator 460. Interconnections 470, 480 and 490 are computer/data connection systems used to transmit and receive data between devices. Interconnections 470, 480 and 490 may be implemented using, but not limited to, the following techniques; RS-232, RS-422, RS-423, RS-488, AppleTalk, LocalTalk, Ethernet, wireless Ethernet, 802.11.

Figure 5:
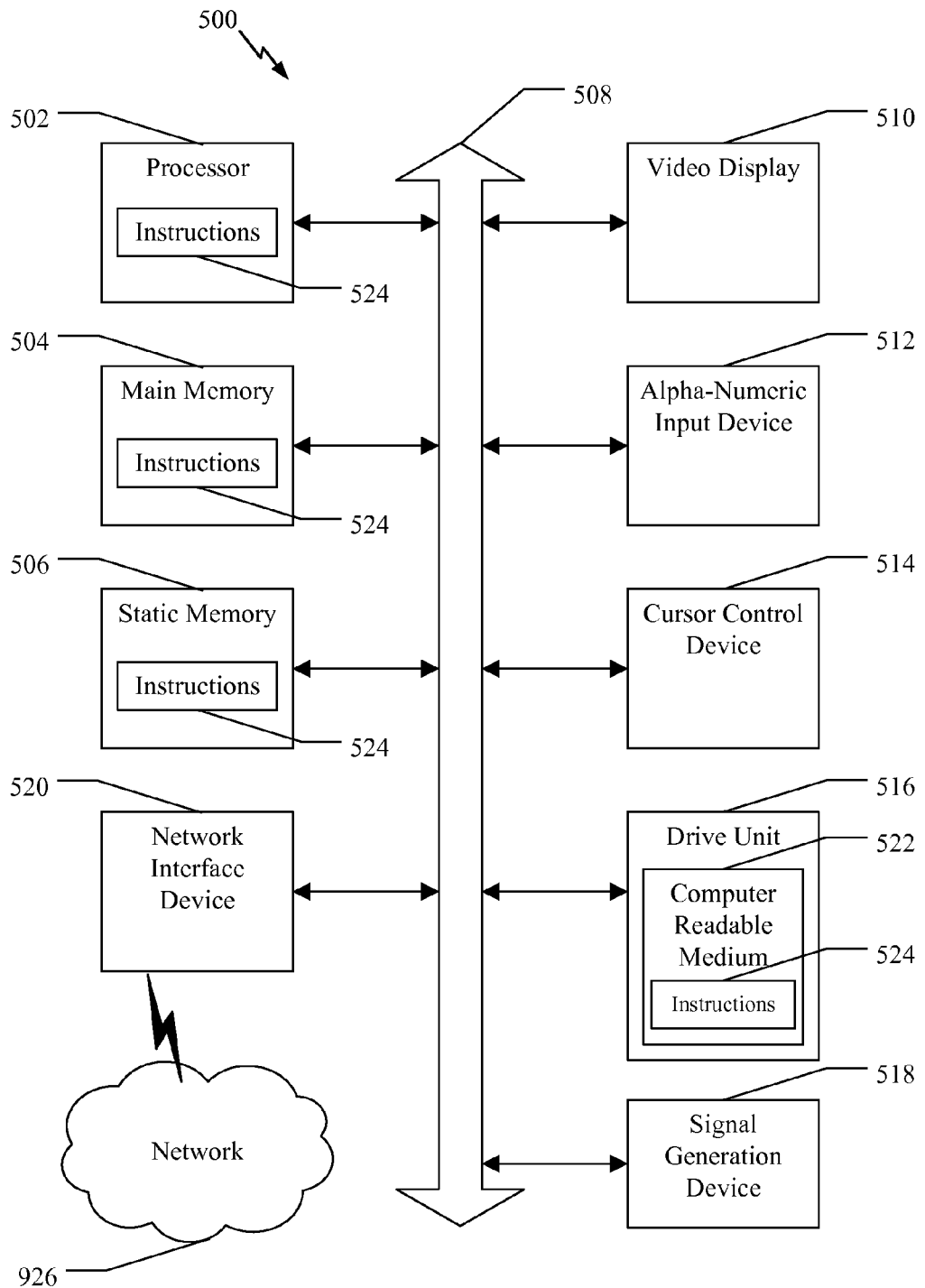
FIG. 5 is a block diagram of an illustrative embodiment of a general computer system.

Referring to FIG. 5 an illustrative embodiment of a general computer system is shown and is designated 500. The computer system 500 can include a set of instructions that can be executed to cause the computer system 500 to perform any one or more of the methods or computer based functions disclosed herein. The computer system 500, or any portion thereof, may operate as a standalone device or may be connected, e.g., using a network, to other computer systems or peripheral devices.

In a networked deployment, the computer system may operate in the capacity of a server, such as a video server or application server, or a media device. The computer system 500 can also be implemented as or incorporated into various devices, such as a personal computer (PC), a personal digital assistant (PDA), a mobile device, a palmtop computer, a laptop computer, a desktop computer, a communications device, a wireless telephone, a web appliance, a network router, switch or bridge, or any other machine capable of executing a set of instructions (sequential or otherwise) that specify actions to be taken by that machine. In a particular embodiment, the computer system 500 can be implemented using electronic devices that provide voice, video or data communication. Further, while a single computer system 500 is illustrated, the term "system" shall also be taken to include any collection of systems or sub-systems that individually or jointly execute a set, or multiple sets, of instructions to perform one or more computer functions.

As illustrated in FIG. 5, the computer system 500 may include a processor 502, e.g., a central processing unit (CPU), a graphics-processing unit (GPU), or both. Moreover, the computer system 500 can include a main memory 504 and a static memory 506 that can communicate with each other via a bus 508. As shown, the computer system 500 may further include a video display unit 510, such as a liquid crystal display (LCD), a flat panel display, a solid-state display, or a cathode ray tube (CRT). Additionally, the computer system 500 may include an input device 512, such as a keyboard, and a cursor control device 514, such as a mouse. The computer system 500 can also include a disk drive unit 516, a signal generation device 518, such as a speaker or remote control, and a network interface device 520.

In a particular embodiment, as depicted in FIG. 5, the disk drive unit 516 may include a computer-readable medium 522 in which one or more sets of instructions 524, e.g. software, can be embedded. Further, the instructions 524 may embody one or more of the methods or logic as described herein. In a particular embodiment, the instructions 524 may reside completely, or at least partially, within the main memory 504, the static memory 506, and/or within the processor 502 during execution by the computer system 500. The main memory 504 and the processor 502 also may include computer-readable media.

Those of skill would further appreciate that the various illustrative logical blocks, configurations, modules, circuits, and algorithm steps described in connection with the embodiments disclosed herein may be implemented as electronic hardware, computer software, or combinations of both. To clearly illustrate this interchangeability of hardware and software, various illustrative components, blocks, configurations, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The steps of a method or algorithm described in connection with the embodiments disclosed herein may be embodied directly in hardware, in a software module executed by a digital signal processor, microprocessor, or in any combination thereof. A software module may reside in random access memory (RAM), flash memory, read-only memory (ROM), programmable read-only memory (PROM), erasable programmable read-only memory (EPROM), electrically erasable programmable read-only memory (EEPROM), registers, hard disk, a removable disk, a compact disc read-only memory (CD-ROM), or any other form of storage medium known in the art. An exemplary storage medium is coupled to the processor such that the processor can read information from, and write information to, the storage medium. In the alternative, the storage medium may be integral to the processor. The processor and the storage medium may reside in an application-specific integrated circuit (ASIC). The ASIC may reside in a computing device or a user terminal. In the alternative, the processor and the storage medium may reside as discrete components in a computing device or user terminal.

The previous description of the disclosed embodiments is provided to enable any person skilled in the art to make or use the disclosed embodiments. Various modifications to these embodiments will be readily apparent to those skilled in the art, and the principles defined herein may be applied to other embodiments without departing from the scope of the disclosure. Thus, the present disclosure is not intended to be limited to the embodiments shown herein but is to be accorded the widest scope possible consistent with the principles and novel features as defined by the following claims.

What is claimed is:

1. A method to analyze a spread of viral or bacterial infections in a population using remote thermal sensor data:
   determining a body temperature of at least one passenger traveling through a public transportation facility using a remote thermal sensor;
   storing the body temperature of the at least one passenger in a database;
   assigning at least one geographic characteristic to the stored body temperature in the database;
   comparing the body temperature of the at least one passenger to a known normal body temperature of humans; and
   comparing relative body temperatures of passengers from one specific point of departure with passengers from a different point of departure.

2. The method of claim 1, further comprising generating an alert when the body temperature of the at least one passenger is above the normal body temperature to indicate an illness.

3. The method of claim 2, wherein the at least one geographic characteristic is an origination location, destination location, or any combination thereof.

4. The method of claim 3, further comprising:
   determining the at least one geographic characteristic by accessing flight information stored on a remote server; and correlating the flight information to the at least one passenger.

5. The method of claim 4, further comprising adjusting the known normal body temperature of humans based on a time of day when determining the body temperature of the at least one passenger traveling through the public facility.

6. The method of claim 5, wherein the known normal body temperature is increased for afternoon and evening time of day over morning time of day.

7. The method of claim 6, further comprising comparing the relative body temperatures of passengers from one specific point of departure with passengers from the same point of departure who arrived earlier or later.

8. The method of claim 7, further comprising:
comparing the relative body temperatures of passengers from multiple points of departure; and
collating a percentage of passengers from varying points of departure with variations in body temperature.

9. The method of claim 8, further comprising comparing body temperature with a relative seating of passengers within an aircraft.

10. A non-transitory processor readable medium having processor instructions that are executable to cause a processor to:
determine a body temperature of at least one passenger traveling through a public facility using a remote thermal sensor;
store the body temperature of the at least one passenger in a database;
assign at least one geographic characteristic to the stored body temperature in the database;
compare the body temperature of the at least one passenger to a known normal body temperature of humans;
wherein the processor executable instructions are further executable to compare relative body temperatures of passengers from one specific point of departure with passengers from a different point of departure.

11. The non-transitory processor readable medium of claim 10, wherein the processor executable instructions are further executable to generate an alert when the body temperature of the at least one passenger is above the normal body temperature to indicate an illness.

12. The non-transitory processor readable medium of claim 11, wherein the at least one geographic characteristic is an origination location, destination location, or any combination thereof.

13. The non-transitory processor readable medium of claim 12, wherein the processor executable instructions are further executable to:
determine the at least one geographic characteristic by accessing flight information stored on a remote server; and
correlate the flight information to the at least one passenger.

14. The non-transitory processor readable medium of claim 13, wherein the processor executable instructions are further executable to adjust the known normal body temperature of humans based on a time of day when determining the body temperature of the at least one passenger traveling through the public facility.

15. The non-transitory processor readable medium of claim 14, wherein the known normal body temperature is increased for afternoon and evening time of day over morning time of day.

16. The non-transitory processor readable medium of claim 15, wherein the processor executable instructions are further executable to compare the relative body temperatures of passengers from one specific point of departure with passengers from the same point of departure who arrived earlier or later.

17. A system to analyze a spread of viral or bacterial infections in a population using remote thermal sensor data, the system comprising:
a remote thermal sensor to collect body temperatures of passengers traveling through a public transportation facility;
a database to store the body temperatures;
a tracking module to track an origination location, destination location, or any combination thereof, of the passengers;
a correlation module to correlate the body temperatures to the origination location, destination location, or any combination thereof, of the passengers; and
an analysis module to predict trends of viral or bacterial infections based on the body temperatures and the origination location, destination location, or any combination thereof, of the passengers;
wherein the correlation module compares relative body temperatures of passengers from one specific point of departure with passengers from a same point of departure who arrived earlier or later.

* * * * *